United States Patent [19]

Nelson et al.

[11] Patent Number: 4,690,963

[45] Date of Patent: Sep. 1, 1987

[54] TARTRATE-BASED LIGHT STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[21] Appl. No.: 902,781

[22] Filed: Sep. 2, 1986

Related U.S. Application Data

[63] Continuation of Ser. No. 786,797, Oct. 11, 1985, abandoned.

[51] Int. Cl.$^4$ ............... C07D 401/12; C07D 401/14; C08K 5/34
[52] U.S. Cl. ..................................... 524/98; 524/103; 524/102; 540/543; 546/19; 546/187
[58] Field of Search ................. 546/19, 187; 524/102, 524/103, 98; 540/543

[56] References Cited

U.S. PATENT DOCUMENTS 4,608,436  8/1986  Cantatore et al. ................... 546/19

Primary Examiner—Robert T. Bond
Attorney, Agent, or Firm—Richard A. Rowe

[57] ABSTRACT

Monomeric and oligomeric derivatives of the diethyl ester of polyalkyl 1,4-dioxa-8-azaspiro-[4.5]-decane-2,3-dicarboxylic acid are useful light stabilizers for synthetic polymer resins such as polyolefins, and in particular, polypropylene.

12 Claims, No Drawings

TARTRATE-BASED LIGHT STABILIZERS FOR PLASTICS

This is a continuation of co-pending application Ser. No. 786,797, filed on Oct. 11, 1985, now abandoned.

The invention is directed to polymeric compositions which are resistant to degradation when exposed to actinic radiation. In particular, it is directed to resins such as polypropylene stabilized with effective amounts of cyclic acetals of aldehydes and ketones containing the polyalkylpiperidine moiety. The invention is further directed to a novel group of substances which are useful as additives for synthetic polymers which act to retard photodegradation.

Many synthetic organic polymers deteriorate rapidly when exposed to sunlight. To circumvent this rapid degradation many additives have been developed to stabilize these resins against the harmful radiation. These additives include hydroxybenzophenones, hydroxybenzotriazoles, organonickel complexes and a number of compounds which incorporate a hindered amine, such as 2,2,6,6-tetraalkylpiperdine, that is substituted in the 4-position. However, because none of these compounds sufficiently satisfy the stabilization requirements of a polymers in their wide variety of forms and applications, there remains a need for new substances which are more satisfactory.

The polymer compositions of the invention are made by the incorporation of an effective amount of a hindered piperidone compound having the formula I with the resin to be stabilized. These compounds may be selected from those structures described by formula I which appears in the Table of Structures, wherein n has a value of 1 to 15. When n is 1, p and q can be 1 or 0; when n is greater than 1, p is 1, while q may be 1 or 0.

$R'$ is selected from hydrogen and an alkyl group of 1 to 5 carbon atoms preferably hydrogen and methyl, and especially hydrogen, $R^2$ is selected from hydrogen, oxyl, hydroxyl, a straight or branched chain methylene-linked alkyl group from 1 to 18 carbon atoms such as methyl, ethyl, octyl, octadecyl, or 2-ethylhexyl, an alkanoyl group having 2 to 18 carbon atoms such as acetyl, propanoyl, butanoyl, isopentanoyl, or stearoyl, an alkenyl group of 3-4 carbon atoms, an alkenoyl group having 3 to 6 carbon atoms such as acryloyl, methacryloyl, crotonyl, 2,3-dimethylcrotonyl, an alkynyl group having 3 to 6 carbon atoms such as propargyl or 2-butynyl, a cyanomethyl group, a 2,3-epoxypropyl group, an unsubstituted or substituted aralkyl group of 7 to 15 carbon atoms such as 3,5-di-tert-butyl-4-hydroxybenzyl, 3-tert-butyl-4-hydroxybenxyl, or 3-tert-butyl-4-hydroxy-5-methylbenzyl, a group —$CH_2CH(OR^5)$—$R^6$, and a group of the formula

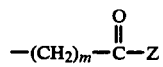

where Z is a group selected from —$OR^7$ and —$N(R^8)(R^9)$ and m is either 1 or 0 and when m is 0, Z can be a group —C(O)—$OR^{10}$; and —A—C(O)—$R^{11}$, $R^3$ and $R^4$, same or different, are selected from an alkyl group of 1 to 18 carbon atoms such as $R^2$, hydrogen and a group of formula II, $R^5$ is selected from hydrogen, an aliphatic group of 1 to 18 carbon atoms such as those of $R^2$, and araliphatic group such as benzyl and phenethyl, and an aliphatic acyl group of 2 to 18 carbon atoms such as those of $R^2$, $R^6$ is selected from hydrogen, an alkyl group of 1 to 16 carbon atoms such as those of $R^2$, and phenyl, $R^7$ is selected from an alkyl group of 1 to 18 carbon atoms, a cycloalkyl group of 5 to 12 carbon atoms such as cyclopentyl, cyclohexyl, cyclooctyl, and cyclododecyl, allyl, benzyl, phenyl, and a group of formula II wherein $R'$ and $R^2$ are as described above, $R^8$ and $R^9$, same or different, are selected from hydrogen, an alkyl group having 1 to 8 carbon atoms such as methyl, ethyl, hexyl, a cycloalkyl group having 5 to 12 carbon atoms such as those of $R^7$, an aryl group having 6 to 10 carbon atoms such as 4-methylphenyl, 2-methylphenyl, 4-butylphenyl, and an aralkyl group having 7 to 15 carbon atoms such as benzyl, o, m, and p-alkylsubstituted benzyl, and phenethyl, and $R^8$ and $R^9$ together with the nitrogen atom to which they are attached can form a 5 to 7-membered ring such as pyrrolidine, piperidine and homopiperidine, $R^{10}$ is selected from an unsubstituted alkyl group of 1 to 18 carbon atoms, phenyl and benzyl and is preferably $C_{1-2}$ alkyl, A is selected from a straight or branched chain alkylene group of 1 to 12 carbon atoms, phenylene and a group —NH—$R^{12}$—NH—where $R^{12}$ is selected from an alkylene group of 2 to 18 carbon atoms, either straight chained or branched, a cycloalkylene group having 5 to 18 carbon atoms, an arylene group having 6 to 18 carbon atoms, and an aralkylene group having 7 to 18 carbon atoms and $R^{11}$ is a group of the formula III, X is either —O—or —$NR^{13}$ where $R^{13}$ is selected from hydrogen or an alkyl group of 1 to 8 carbon atoms such as methyl, ethyl, butyl or octyl.

Y is a divalent alkylene group having 2-20 carbon atoms, either straight-chained or branched, wherein the alkylene may be interrupted by —O—, —S— or —$NR^{13}$. Also Y may be selected from a cycloalkylene group of 6-12 carbon atoms such as cyclohexanyl and cycloctanyl and dialkanylcycloalkane such as dimethanocyclohexane, diethanocyclohexane, dicyclohexanylmethane, dicyclohexanylethane, dimethanocyclohexylmethane, diethanocyclohexylmethane, diethanocyclohexylethane, 2,2-dicyclohexanylpropane, a phenylene group and an aralkylene group having 8 to 15 carbon atoms such as dimethanobenzene and 4,4'-isopropylidenediphenyl. The compounds and oligomers represented by formula I may range in molecular weight from about 320 to 10,000.

The compounds of formula I may be prepared in a single or a multistep process. The first step in the process (n is 1, p and q are 0 and X is —O—) is the preparation of the acetal derived from the diol

and a 4-oxopolyalkylpiperidine of the formula IV, using a suitable acid catalyst and a suitable solvent as generally known in the art for the preparation of acetals. Examples of suitable acid catalysts are numerous, however, without introducing any limitations are mentioned p-toluenesulfonic acid and methanesulfonic acid. Examples of suitable solvents are cyclohexane and benzene. Although $R^3$ and $R^4$ may be any alkyl group of 1 to 18 carbon atoms for this reaction it is preferred that they be the same and that they be ethyl or methyl.

These diols also known as diethyl tartrate and dimethyl tartrate are available commercially.

The reaction of 2,2,6,6-tetraalkyl-4-piperdones with dihydroxy substances to form the corresponding acetal derivatives is well-known and techniques similar to those described in U.S. Pat. Nos. 3,790,525; 3,899,464: 4,007,158; 4,105,626; and EP No. 22,997 may be employed. Of particular interest as a starting component is 2,2,6,6-tetramethyl-4-piperidone. Preparative procedures for this ketone may be found throughout the literature and in U.S. Pat. No. 4,105,626, Column 9. Specifically the compound is prepared by reaction of ammonia with acetone.

The preparation of other polyalkylpiperidin-4-ones of formula IV can be prepared by reaction of ammonia with an aliphatic ketone such as methyl ethyl ketone. This procedure has been described by W. Traube in Chem. Ber. 41,777 (1908).

Compounds of the formula IV which carry other alkyl substitutents in the 2-position and the 6-position can be prepared in a two step process following the procedures outlined in Helv. Chim. Acta 30, 1114(1947) and Montash. Chem. 88,464(1957), followed by hydrolysis of the resulting pyrimidine.

The acetalization reaction is generally carried out in refluxing solution of a water-immiscible solvent at a temperature of about 80° C. in the presence of an acid catalyst. Solvents which work well are 1,2-dichloroethane and chlorbenzene as well as others that may be useful. Acid catalysts which work well are 1,2-dichloroethane and chlorobenzene as well as others that may be useful. Acid catalysts which are commonly utilized are organic acids such as methanesulfonic acid, paratoluenesulfonic acid and others which are considered useful. The acetal which forms is generally isolated by solvent extraction and after concentration can be purified by distillation or crystallization.

The diethyl or dimethyl spiroacetal can be used as a starting material for the second step in the process. Higher molecular weight monomeric esters and amides can be prepared by reaction of the diethyl spiroacetal, neat or in solution, with higher molecular weight monofunctional alcohols, amines or mixtures thereof using a basic catalyst like lithium amide or titanium tetraisopropoxide. Oligomers and polymers wherein n is greater than 1 up to a value of about 15 and preferably having a value of 2 to 10 may be formed under similar conditions employing difunctional alcohols, amines or mixtures thereof.

The products may be separated from solvent solution and are generally purified by trituration or crystallization or any other suitable procedure.

The 4-hydroxypolyalkylpiperidines and the 4-aminopolyalkylpiperidines used to convert the acetals into the compounds of the invention are known from German patent No. 2,352,658 and U.S. Pat. No. 3,684,765. In general, the 4-hydroxy compounds are prepared from the corresponding 4-oxopiperidines by reduction via catalytic hydrogenation over Raney Nickel and the 4-amino compounds are synthesized via a reductive amination using ammonia or the particular primary amine of interest.

The introduction of an alkyl, alkenyl, alkynyl, aralkyl and 2,3-epoxypropyl group can be achieved by reaction of the initially prepared acetal containing the free N-H of the polysubstituted piperidine with suitable halides like methyl iodide, ethyl bromide, propyl bromide, dodecyl chloride, and octadecyl chloride: allyl bromide, methallyl chloride, butenyl chloride, propargyl bromide, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

The introduction of an alkanoyl or an alkenoyl group can be performed by acylation of the parent N-H compound using the suitable acid halide or, when convenient, the acid anhydride. If the acid halide is used the generated hydrogen halide can be scavenged in the same manner as stated previously. Examples of such groups are acetyl chloride, propionyl chloride, hexanoyl chloride, dodecanoyl chloride, octadecanoyl chloride, acetic anhydride, and propionic anhydride. Similarly the oxalyl chloride monoester can be introduced using reagents such oxalyl chloride monomethyl ester and oxalyl chloride monoethyl ester.

For the compound when $R^2$ is the group $-CH_2CH(OR^5)-R^6$ the substituent can be introduced by reaction of the parent N-H compound with the corresponding alkylene oxide such as ethylene oxide, propylene oxide and stryene oxide. The resulting hydroxy compound can be acylated in the manner commonly known in the art using the suitable acid halide and can be alkylated by generating the alkoxide using a base like sodium hydride and treating it with the desired alkyl or aralkyl halide.

When $R^2$ is the group and $-CH_2-_mCOZ$ is zero the appropriate group can be attached by reacting the parent N-H compound with a chloroformate such as methyl chloroformate, ethyl chloroformate, allyl chloroformate, hexylchloroformate, decyl chloroformate, octadecyl chloroformate, and phenyl chloroformate.

For preparation of the corresponding ureas the parent N-H compound can be treated with the suitable carbamyl halide such as methyl carbamyl chloride, ethyl carbamyl chloride, butyl carbamyl chloride, phenyl carbamyl chloride, dimethyl carbamyl chloride, diethylcarbamyl chloride, dihexylcarbamyl chloride, pyrrolidinyl carbamyl chloride, piperidine carbamyl chloride, and homopiperidine carbamyl chloride. Alternatively, the ureas can be prepared by treating the parent N-H compound with the suitable isocyanate. The bis-ureas can be prepared using the suitable diisocyanate.

Compounds of formula I wherein $R^2$ is the oxyl radical are obtainable from the corresponding N-H compounds by oxidation with a peroxide such as hydrogen peroxide in the presence of a catalyst like sodium tungstate or with percarboxylic acids like metachloroperoxybenzoic acid.

When $R^2$ is the group $-(CH_2)_m-COZ$ and m is 1 the appropriate group can be attached by reacting the parent N-H compound with an ester of chloroacetic acid such as methyl chloroacetate, ethyl chloroacetate, chyclohexychloroacetate, benzyl chloroacetate, allyl chloroacetate and phenyl chloroacetate.

The compounds of this invention are effective light stabilizers for synthetic organic polymers.

The following examples are given to illustrate but not limit the invention.

EXAMPLE 1

7,7,9,9-Tetramethyl-1,4-dioxa-8-azaspiro-[4.5]decane-2,3-dicarboxylic acid, diethyl 1 ester To a mixture of diethyl tartrate (15.0 g, 72.8 mmol) and triacetoneamine hydrate (12.6 g, 72.8 mmol) in 100 ml of 1,2-dichloroethane was added the methane sulfonic acid (13.95 g, 145 mmol) in another 50 ml of solvent. The mixture was heated to reflux and maintained for 96 h. with azeotropic removal of the generated water and incremental additions of further acid (13.95 g). The mixture was then cooled to ambient temperature, the acid neutralized with dilute aqueous sodium hydroxide and subsequently washed with water. Drying and concentration yielded 18.9 g (75%) of an orange viscous liquid. Purification by removal of triacetoneamine and molecular distillation (140° C. @0.25 mm) yielded 9.29 g (37%) of the desired substance as a light yellow material.

EXAMPLE 2

7,7,9,9-Tetramethyl-1,4-dioxa-8-azaspiro-[4.5]decane-2,3-dicarboxylic acid, diester with 2,2,6,6-tetramethylpiperidin 4-ol To a mixture of the product of Example 1 (4.24 g, 12.3 mmol) and 2,2,6,6-tetramethylpiperidin-4-ol (4.09 g, 26.0 mmol) in 70 ml of ligroine at reflux and under a gentle stream of nitrogen was added the lithium amide (30 mg) as catalyst. The mixture was maintained at reflux with intermittent drainage of the collected solvent from the Dean-Stark trap and replacement with an equivalent amount of fresh solvent. After 17 h. the reaction mixture was cooled, the catalyst was neutralized with acetic acid (90 mg) and diluted with additional ligroine and filtered. Concentration in vacuo yielded a yellow, viscous liquid which when freed from unreacted alcohol weighed 6.27 g (90%) having general formula $C_{31}H_{55}N_3O_6$.

EXAMPLE 3

7,7,9,9-Tetramethyl-1,4-dioxa-8-azaspiro-[4.5]decane-2,3-dicarboxylic acid, oligomeric with 2,2-dimethyl-1,3-propanediol A mixture of the compound of Example 1 (4.83 g, 14.0 mmol) and 2,2-dimethyl-1,3-propanediol (1.46 g, 14.0 mmol) under a gentle nitrogen stream was heated to 120° C. The catalyst lithium amide (38 mg) was then added. The pressure was reduced to about 60 mm and the evolved ethanol was collected. After 15 minutes at 120° C. the temperature was increased to 150° C. and maintained for an additional 2 hours. The mixture was then cooled, dissolved with methylene chloride and the catalyst was neutralized with acetic acid (100 mg). The organic solution was washed with brine and water which upon isolation yielded 4.4 g (88%) of a tan foam.

EXAMPLE 4

7,7,9,9-Tetremethyl-1,4-dioxa-8-azaspiro-[4.5]decane-2.3-dicarboxylic acid, oligomeric with 1,6-hexane diamine A mixture of the compound of Example 1 (3.43 parts) and 1,6-hexanediamine (1.18 parts) was heated at 150° C. in the presence of lithium amide and maintained for 18 hours. The crude reaction mixture was cooled, dissolved in methylene chloride and washed with water. The organic solution was dried (sodium sulfate) and concentrated. The product was consistent with that desired as evidenced by MNR spectroscopy.

The spiroacetal derivatives of the invention are particularly useful as light stabilizers for synthetic polymers which undergo degradation in the presence of air and actinic radiation. As used herein polymers are intended to embrace polyolefins including homopolymers of olefins such as low density and high density polyethylene, polypropylene, polystyrene, polybutadiene, polyisoprene and the like; and copolymers of olefins with other ethylenically unsaturated monomers such as ethylene-propylene copolymer, ethylene-butylene copolymer, ethylene-vinyl acetate copolymer, styrene-butadiene copolymer, acrylonitrile-styrene-butadiene copolymer and the like; polyvinyl chlorides and polyvinlidene chlorides including homopolymers of each of vinylchloride and vinylidene chloride, vinylchloride-vinylidene copolymers and copolymers of each vinylchloride and vinylidene chloride wit vinyl acetate or other ethylenically unsaturated monomer; polyacetal as such polyoxymethylene and polyoxyethylene; polyesters such as polyethyleneterephthalalte; polyamide such as 6-nylon, 6,6-nylon and 6,10-nylon and polyurethanes Z and polymers derived from $\alpha,\beta$-unsaturated acids and derivatives thereof, polyacrylates and polymethacrylates, polyacrylic amides and polyacrylonitrile, as well as copolymers of acrylic acid and one or more of its derivatives with a melamine-formaldehyde resin.

Synthetic polymers have been widely utilized in the art in view of their excellent properties in various forms or shapes, for example, filaments, fibers, yarns, filament sheet, other molded articles and other molded articles made from latex and foam. However, these polymers have some drawbacks such as poor light and heat stabilities among others. Stated illustratively, pololefins and polyurethane elastomers frequently tend to undergo sever deterioration when exposed to light such as sunlight or ultraviolet light and polyvinyl chloride and polyvinylidene chlorides frequently tend to deteriorate and become colored by the action of light and heat together with elimination of hydrogen chloride. Polyamides are also frequently subjected to photodegradation. For the purpose of stabilizing these synthetic polymers against such degradation, these have been proposed in the art a number of stabilizers. For example, in the case of polyolefins, benzotriazole and benzophenone compounds; for polyurethanes, phenol compounds and benzophenone compounds; and for polyvinylchlorides and vinylidene chlorides, lead salts such as basic lead silicate and trisilicate, lead maleate and organic tin compounds such as dibutyltinlaurate and dibutyltinmaleate.

The resin should have incorporated within an effective stabilizing amount of a compound described by formula I. The amount will depend upon the nature of the plastic and the amount of radiation to which the plastic will be subject. Generally an amount between about 0.01% and 5.0% by weight of the polymer is effective. Preferably they may be used in concentrations between 0.05 and 1% by weight.

In addition, the light stabilizers of formula I may be used with fillers and additional stabilizers including antioxidants, flame retardant stabilizers, anti-slipping and antistatic agents, supplemental light stabilizers, pigments, dyes, lubricants, etc.

Suitable antioxidants include those of the hindered phenol type such as 2,6-di-t-butyl-p-cresol; 4,4'-bis(2,6-di-t-butylphenol); 4,4'-bis(2,6-di-isopropylphenol); 2,4,6-tri-t-butylphenol; 2,2'-thiobis (4-methyl-6-t-butylphenol); octadecyl-2(3 ', 5'-di-t-butyl-4'-hydroxyphenyl propionate: pentaerythrityl tetrakis (3,5-di-t-butyl-4-hydroxyphenylpropionate: 1,3,5-tris(3', 5'-di-t-butyl-4-hydroxybenzyl) isocyanurate; 1,3,5-tris((3',5'-di-t-butyl-4'-hydroxyphenol-propionate) 3',5'-di-t-butyl-4'-hydroxybenzyl)-2,46-dimethylbenzyl) -s-triazine-2,4,6-

(1H,3H,5H)-trione and esters of thiodipropionic acid such as dilaurylthiodipropionate and distearylthiodipropionate etc.; hydrocarbyl phosphites such as triphenyl phosphite, trinonyl phosphite, didodecyl pentaerythrityl diphosphite, diphenyldecyl phosphite, tris-(2,4-di-t-butylphenyl)phosphite, bit(2,4-di-t-butylphenyl)pentaerythritol diphosphite, etc, in combinations thereof.

Suitable supplemental light stabilizers include those of the benzotriazole class, such as 2-(2'-hydroxy-5-5-oxtylphenyl benzotriazole; 2,(2'-hydroxy-3',5'-di-t-butyl-phenyl)-5-chlorobenzotriazole: 2-(2'-hydroxy-3'-t-butyl-5'-methylphenyl)5-chlorobenzotriazole; 2-(2'-hydroxy-3'-t-butyl-5'-methylphenyl)-5-chlorobenzptriazole; 2-(2'-hydroxy)-3', 5 '-di-t-amylphenyl)-benzotriazole: those of the hydroxybenzophenone type such as 2-hydroxy-4-methoxybenzophenone; 2-hydroxy-4-octyloxybenzophenone; 2,2'-dihydroxy-4,4'-di-methoxybenzophenone; hindered phenol esters, such as n-hexadecyl3,5-di-t-butyl-4-hydroxybenzoate, and 2',4'-di-t-butylphenol-3, 5-di-t-butyl-4-hydroxybenzoate; methyl complexes such as nickel complexes of 2,2'-thiobis(4-6-octylphenol), nickel butylamine complexes of 2,2'-thiobis(4-t-octyl-phenol); nickel butylamine complexes of 2,2'-thiobis(4-t-octylphenol); nickle complexes of bis (4-t-octyl-phenol)sulphone nickel dibutyl thiocarbamate; nickel salts of 4-hydroxy-3,5-di-t-butylbenzylphosphonic acid monoalkyl esters where alkyl is methyl, ethyl, propoyl, butyl etc.; nickel complexes of to 2-hydroxy-4-methylphenyl undecylketoneoxime. Further illustrative examples of suitable antioxidants of supplemental light stabilizers can be found in columns 3 and 4 of U.S. Pat. Nos. 3,488,290 and 3,496,134.

EXAMPLES 5-7

In order to illustrate the effectiveness of the above-described compounds as light stabilizers the previously described materials of Examples 1-5 are each incorporated into a commercially available polypropylene resin manufactured by Hercules Corporation as PRO-FAX ™ 6301 Polypropylene Resin. The light stabilizers may be incorporated with the polypropylene by solvent blending (methylene chloride) at concentrations of 0.25% by weight of the total resin composition and as a primary antioxidant, stearyl β-3,5-di-t-butyl-4-hydroxyphenylpropionate is used at a concentration of 0.2%. The resin is then extruded at 200° C. and compression molded at 6,000 psi at 188° C. to produce films having thicknesses of 5 mils. Each test film and control film is exposed to Xenon Arc in an Atlas weather-o-meter until the infrared carbonyl adsorption increased by 0.5, which is considered to be the failure point. Time-to-failure is expected to be 8-10 times that of the control having no stabilizer.

TABLE OF STRUCTURES

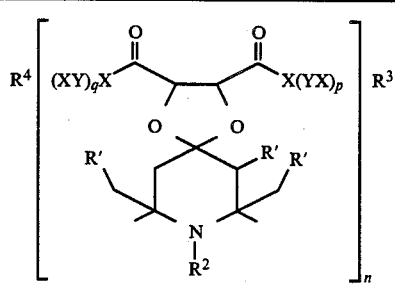

I

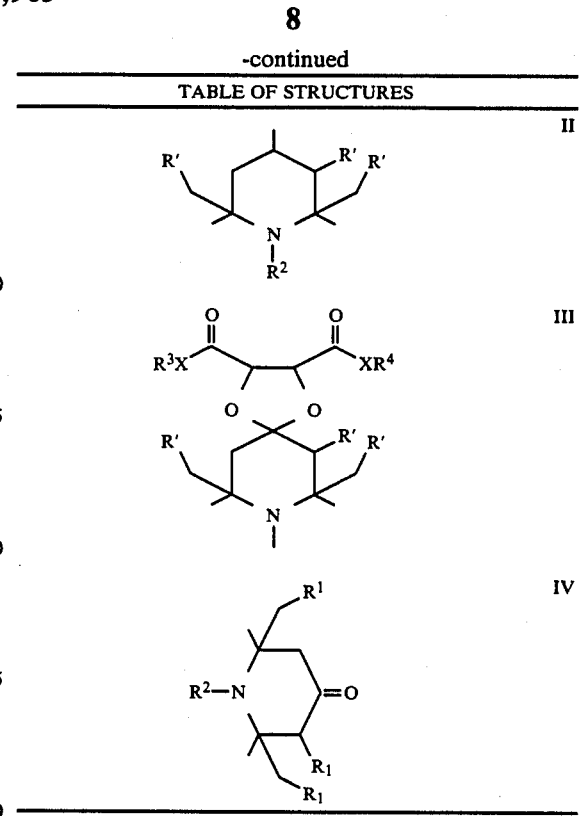

What is claimed is:
1. A compound of the formula I
wherein n has a value of 1 to 15,
when n is 1, p and q can be 1 or 0, when n is greater than 1, p is 1, while q may be 1 or 0;
R' is selected from hydrogen and an alkyl group of 1 to 5 carbon atoms;
$R^2$ is selected from hydrogen, oxyl, hydroxyl, a methylene-linked alkyl group from 1 to 18 carbon atoms, an alkanoyl group having 2 to 18 carbon atoms, an alkenyl group of 3 to 4 carbon atoms, an alkenoyl group having 3 to 6 carbon atoms, an alkynyl group having 3 to 6 carbon atoms, a cyanomethyl group, a 2,3-epoxypropyl group, an aralkyl group of 7 to 15 carbon atoms, a group —$CH_2CH(OR^5)$—$R^6$, and a group of the formula

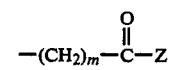

where Z is a group selected from —$OR^7$ and —$N(R^8(R^9))$ and m is either 1 or 0 and when m is 0, Z is a group —$C(O)$—$OR^{10}$ and —A—$C(O)$—$R^{11}$;
$R^3$ and $R^4$, same or different are selected from an alkyl group of 1 to 18 carbom atoms such as $R^2$, hydrogen and a group of formula II;
$R^5$ is selected from hydrogen, a methylene-linked alkyl group from 1 to 18 carbon atoms, an alkanoyl group having 2 to 18 carbon atoms, an alkenyl group of 3 to 4 carbon atoms, an alkenoyl group having 3 to 6 carbon atoms, an alkynyl group having 3 to 6 carbon atoms, a cyanomethyl group, a 2,3-epoxypropyl group, an aralkyl group of 7 to 15 carbon atoms;
$R^6$ is selected from hydrogen, an alkyl group of 1 to 16 carbon atoms such as those of $R^2$, and phenyl;

R[7] is selected from an alkyl group of 1 to 18 carbon atoms, a cycloalkyl group of 5 to 12 carbon atoms alkyl, benzyl, phenyl, and a group of formula III wherein R' and R[2] are as described above;

R[8] and R[9], same or different, are selected from hydrogen, an alkyl group having 1 to 8 carbon atoms, alkyl group having 5 to 12 carbon atoms such as those of R[7], aryl groups having 6 to 10 carbon atoms and aralyl groups having 7 to 15 carbon atoms and R[8] and R[9] together with the nitrogen atom to which they are attached can form a 5 to 7-membered ring selected from the group consisting of pyrrolidine, piperidine and homopiperidine;

R[10] is selected from an unsubstituted alkyl group of 1 to 18 carbon atoms, phenyl and benzyl;

A is selected from an alkylene group of 1 to 12 carbon atoms, phenylene and a group —NH—R[12]—NH—where R[12] is selected from an alkylene group of 2 to 18 carbon atoms, either straight chained or branched a cycloalkylene group having 5 to 18 carbon atoms, an arylene group having 6 to 18 carbon atoms, and an aralkylene group having 7 to 18 carbon atoms and R[11] is a group of the formula III;

X is either —O— or —NR[13] where R[13] is selected from hydrogen or an alkyl group of 1 to 8 carbon atoms;

Y is a divalent alkylene group having 2-20 carbon atoms, wherein the alkylene may be interrupted by —O—, —S— or —NR[13]—, a cycloalkylene group of 6-12 carbon atoms, dialkanylcycloalkane, a phenylene group and an aralkylene group having 8 to 15 carbon atoms whereinsaid formulas are:

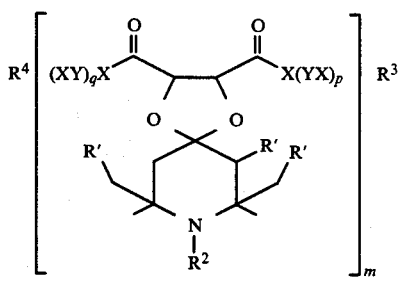

I

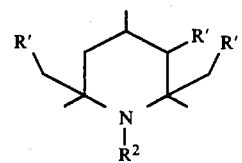

II

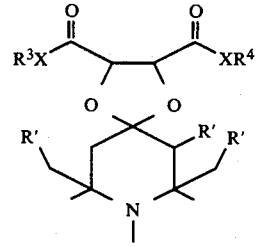

III

2. A compound of claim 1 wherein R' is hydrogen and X is —O—.

3. A compound of claim 2 wherein n has a value of 1 and p and q are 0.

4. A compound of claim 3 wherein R[3] and R[4] are ethyl.

5. A compound of claim 3 wherein R[3] and R[4] are the 2,2,6,6-tetramethyl-4-piperidinyl group.

6. A compound of claim 2 wherein n has a value between 2 and 15 and p and q are 1.

7. A compound of claim 6 wherein n has a value between 3 and 6.

8. A compound of claim 7 wherein Y is the 2,2-dimethyl-1,3-propylene group.

9. A synthetic polymer composition stabilized against light induced deterioration comprising an organic polymer normally subjected to deterioration by light, and from 0.01-5% by weight of a compound of the general formula of claim 1.

10. A composition of claim 9 wherein the organic polymer is a polyolefin homopolymer or copolymer.

11. A composition of claim 10 wherein said organic polymer is a homo or copolymer of polypropylene.

12. A process for the preparation of the compound of claim 4 which comprises heating the dimethyl or diethyl ester of tartaric acid with a polyalkylated 4-piperidone in a refluxing solvent at a temperature less than about 100° C. in the presence of an acid catalyst.

* * * * *